(12) United States Patent  (10) Patent No.: US 8,518,237 B2
Chan et al.  (45) Date of Patent: Aug. 27, 2013

(54) MODULATING POLARIZATION VOLTAGE OF AMPEROMETRIC SENSORS

(75) Inventors: Andy Chan, Franklin, MA (US); Lawrence Milesky, Needham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 164 days.

(21) Appl. No.: 13/119,990

(22) PCT Filed: Sep. 14, 2009

(86) PCT No.: PCT/US2009/056819
§ 371 (c)(1),
(2), (4) Date: Mar. 21, 2011

(87) PCT Pub. No.: WO2010/036529
PCT Pub. Date: Apr. 1, 2010

(65) Prior Publication Data
US 2011/0180426 A1  Jul. 28, 2011

Related U.S. Application Data

(60) Provisional application No. 61/099,370, filed on Sep. 23, 2008.

(51) Int. Cl.
*G01N 27/26* (2006.01)
*G01N 27/404* (2006.01)

(52) U.S. Cl.
USPC .......... 205/783; 73/23.21; 73/1.01; 205/793; 204/415

(58) Field of Classification Search
USPC ................. 205/782.5, 792, 775, 777.5, 783; 204/415; 73/23.21, 1.01
See application file for complete search history.

(56) References Cited

U.S. PATENT DOCUMENTS

| 4,536,274 | A | | 8/1985 | Papadakis et al. |
| 4,571,292 | A | | 2/1986 | Liu et al. |
| 4,900,422 | A | * | 2/1990 | Bryan et al. ................. 204/401 |
| 4,985,123 | A | | 1/1991 | Curley |
| 5,387,329 | A | * | 2/1995 | Foos et al. ................ 204/403.06 |
| 7,336,984 | B2 | | 2/2008 | Gough et al. |
| 2003/0170881 | A1 | | 9/2003 | Davis et al. |
| 2004/0194534 | A1 | | 10/2004 | Porter et al. |

OTHER PUBLICATIONS

International Search Report and Written Opinion for International Application No. PCT/US2009/056819 mailed Nov. 10, 2009.
Chinese Search Report of Chinese Patent Application No. 200980137120.3 dated Nov. 22, 2012.

* cited by examiner

*Primary Examiner* — J. Christopher Ball
*Assistant Examiner* — Jennifer Dieterle
(74) *Attorney, Agent, or Firm* — Noam R. Pollack

(57) ABSTRACT

The service life of amperometric electrochemical oxygen sensors is increased by operating the electrodes of such sensors at a polarization voltage suitable for measuring the oxygen content of samples only during calibration or when measuring such samples and thereafter modulating the polarization voltage to a lower voltage such that substantially no electrical current is produced by the electrodes.

6 Claims, 3 Drawing Sheets

MODULATING POLARIZATION VOLTAGE OF AMPEROMETRIC SENSORS

FIELD OF INVENTION

This invention relates to the operation of electrochemical sensors, particularly amperometric sensors, such as are used to measure oxygen, glucose, lactate and the like, and most particularly to measure the oxygen content of blood.

BACKGROUND OF THE INVENTION

There are several methods of measuring the oxygen concentration of liquids. For medical applications, electrochemical sensors have been developed and marketed. One instrument currently in use is the Rapidpoint 400, available from Siemens Healthcare Diagnostics, Inc. When measuring oxygen content of blood, a sensor of the type described in U.S. Pat. No. 5,387,329 is used. That sensor employs three electrodes, i.e. a working electrode, a reference electrode, and a counter electrode. The general principles of such three electrode sensors are described in U.S. Pat. No. 4,571,292. At the working electrode, oxygen is reduced to hydroxyl ions, while at the counter electrode the hydroxyl ions are oxidized to molecular oxygen. The sensors provide a reversible set of reactions and do not require consumption of the electrodes. The current measured when a voltage is applied across the working and counter/reference electrodes is correlated to the oxygen content of the sample.

Reference may be made to the description in U.S. Pat. No. 5,387,329 for details of a typical oxygen sensor. The three electrodes are thin metal strips deposited on a non-conductive substrate. In the '329 patent, the working electrode is positioned between the counter electrode and the reference electrode. An electrolyte layer, e.g. a Nafion® layer, which is activated when the sensor is in use, covers the electrodes. Next, the electrolyte layer is covered by a membrane that permits oxygen in a sample to diffuse through it to reach the working electrode. It is a feature of the '329 patent's sensor that the working electrode is very small and exhibits rapid non-depleting behavior.

The useful life of such sensors is of great importance, since typically they are available 24 hours a day in hospitals or other clinical settings. The '329 patent teaches that contamination of the membrane by sample components or by other impurities may affect the membrane, shortening its life. Delamination of the sensor components is also considered to be a cause of sensor inaccuracy or failure. Another problem relating to oxygen sensor life has been observed, which is overcome by the present invention.

Experience has shown that, rather than gradually losing accuracy, sensors may suddenly produce a spike in the current output that is unrelated to the oxygen content of the sample being tested, or to the oxygen content of wash or calibration solutions. Unless the current spike is only temporary, the sensor is useless and must be replaced. It is now believed that the current increase is caused by formation of small dendrites extending from the electrodes into the electrolyte layer, which cause an increase in current flow or cause a short circuit between the electrodes. Since the electrodes are quite small, as is the distance between them, it has been difficult to find a solution to this problem, while maintaining the present sensor size.

Contrary to a suggestion in the '329 patent, in a typical operation the sensor is normally polarized at the operating voltage, since it must be calibrated regularly and available for use at all times. After a sample has been tested for its oxygen content, the sensor compartment is washed using an aqueous wash reagent typically containing surfactant to remove the sample and the electrodes remain at the test polarization voltage (e.g. −0.800v) until needed, while remaining in contact with a segment of stagnant wash solution. The segment of wash reagent typically would contain a near ambient level of oxygen or would gradually equilibrate toward an ambient level of oxygen over time. Every 30 minutes, the sensor is tested with calibrating solutions to assure that the sensor is providing accurate results. Thus, the sensor is always kept active and exposed to oxygen in both the segment of stagnant wash and the calibrating solutions. Investigation has shown that this exposure to oxygen contributes to shortening the life of the sensors by the sudden appearance of current spikes as described above. The present invention relates to a means for increasing the life of oxygen sensors and avoiding the sudden appearance of current spikes, as will be described in detail below. The invention also may be applied to other amperometric sensors to improve performance and increase their service life.

SUMMARY OF THE INVENTION

The invention is a method for operating amperometric sensors, such as those used to measure oxygen, glucose, and lactate in blood or the biological fluids. The sensors are only operated at their appropriate polarization voltage when measuring samples for the target constituent (e.g. oxygen). Thereafter, the polarization voltage is modulated to a lower voltage such that substantially no electrical current is produced by the electrodes. Thus, the electrodes are only polarized at the operating voltage when the sensor is to be calibrated or used to test a sample.

The invention in one embodiment is a method of operating electrochemical oxygen sensors in which the sensors are only operated at a polarization voltage suitable for measuring the oxygen content when testing a sample or being calibrated. Thereafter, the polarization voltage is modulated to a lower voltage such that substantially no electrical current is produced by the electrodes. The voltage is only raised to the operating voltage when the sensor is to be calibrated or used to test a sample. Thus, the sensor is polarized at the lower voltage for about 96% of the service life.

In a specific embodiment, the electrochemical sensor has planar electrodes on a substrate, which are covered with a polymer electrolyte and an oxygen-permeable membrane. Oxygen in a sample placed adjacent to the oxygen permeable membrane migrates through the membrane into the electrolyte layer and electrical current is produced by reduction of the oxygen at a working electrode. The current is measured and correlated to the oxygen content of the sample. After testing a sample, the sensor's polarization voltage is reduced while it is being washed. The polarization voltage remains at the reduced level until the sensor is calibrated and used again to test a new sample.

In a preferred embodiment the polarization voltage is about −0.4 to −1.2 volts, preferably about −0.8 volts and the modulated voltage is less than −0.4 volts, preferably about −0.1 volts. The cycling of the polarization voltage is illustrated in FIG. 5.

DESCRIPTION OF THE PREFERRED EMBODIMENTS

The invention generally relates to improving the performance and service life of amperometric sensors, such as are used for measuring oxygen, glucose, lactate, and the like in biological fluids, e.g. blood. In particular, the invention has benefits in analysis of blood for oxygen content, as will be described in detail below.

Amperometric Oxygen Sensing

As described above, an electrochemical oxygen sensor uses electrodes separated by an electrolyte. An oxygen-permeable membrane separates the sample from the electrolyte. When a potential is applied across the electrodes, oxygen from a sample migrates through the membrane into the electrolyte to reach the electrodes, where it is reduced at the working electrode to produce a current. The current is measured and correlated to the oxygen content of the sample. Reference should be made to U.S. Pat. No. 5,387,329 where a typical planar oxygen sensor is shown. A cross sectional view of one embodiment of such an oxygen sensor may be seen in FIG. 1.

Figure 1:
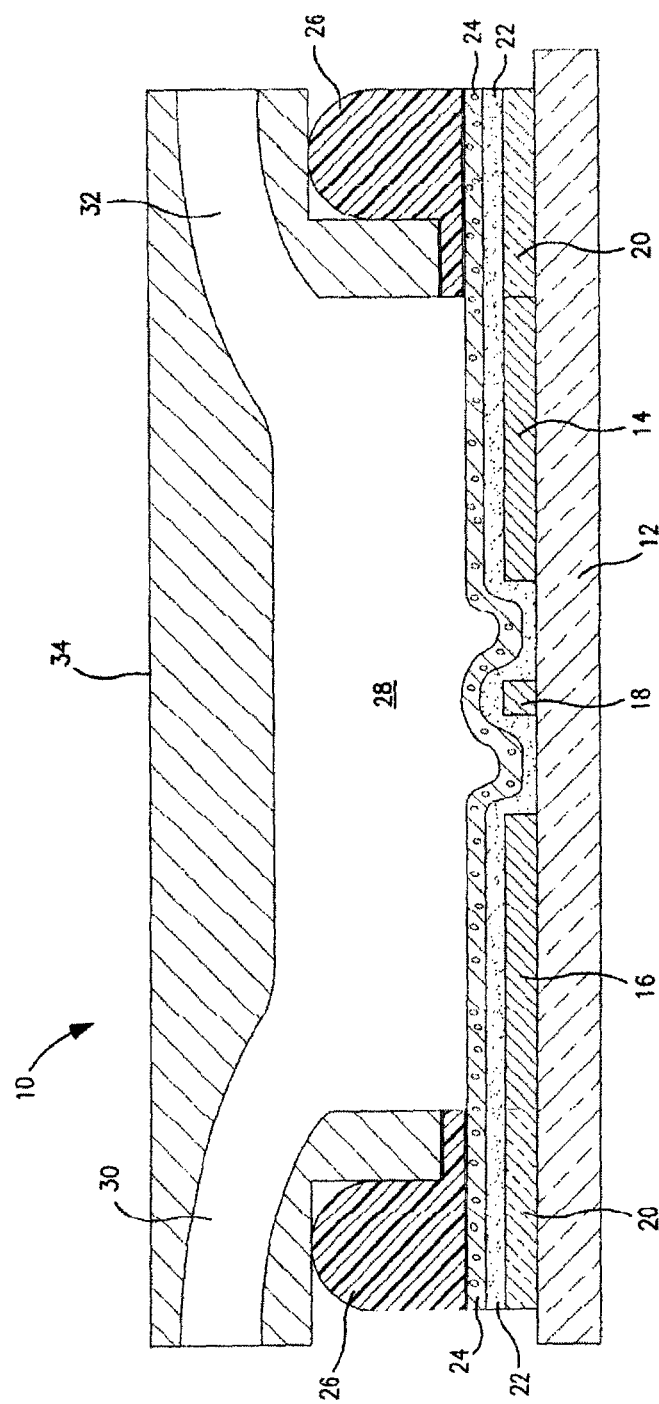
FIG. 1 is a cross-sectional view of an oxygen sensor.

In FIG. 1, the sensor 10 is assembled on a substrate 12. The working electrode 18 is positioned between the reference electrode 14 and the counter electrode 16. Layer 20 is a dielectric layer that contains openings for the electrodes. The electrodes are covered by electrolyte layer 22 (e.g. Nafion®) and permeable membrane 24 (e.g. a copolymer). A sample liquid enters chamber 28 through entry port 30 and exits through exit port 32. Cover 34 encloses the sensor 10. Gasket 26 seals the sample chamber 28 and ports 30 and 32.

As described in the '329 patent, the substrate may be a ceramic insulator. The conductive strips are usually are made by screen printing precious metal (e.g. platinum) pastes on the substrate, the metals being chosen to provide a current plateau when the electrodes are polarized at about –0.8 volts. The electrolyte preferably is a Nafion® polymer. The membrane is a copolymer that has limited permeability to oxygen, but passes water vapor while blocking contaminants that could interfere with sensor performance. The sealing gasket is selected from materials that are gas impermeable and do not contain contaminants.

Such sensors are quite small. In the '329 patent the sample chamber volume is less than 10 μL. The overall dimensions are only about 0.18 inches (4.57 mm) long and 0.18 inches (4.57 mm) wide. The exposed areas of the reference and counter electrodes are only about 16 mm$^2$ each and the working area of the working electrode about 0.01 mm$^2$ The spacing between the working electrodes and the counter and reference electrodes is only about 0.024 inches (0.61 mm) Consequently, the sensors must be very precisely made if they are to provide consistently accurate results.

Figure 2:
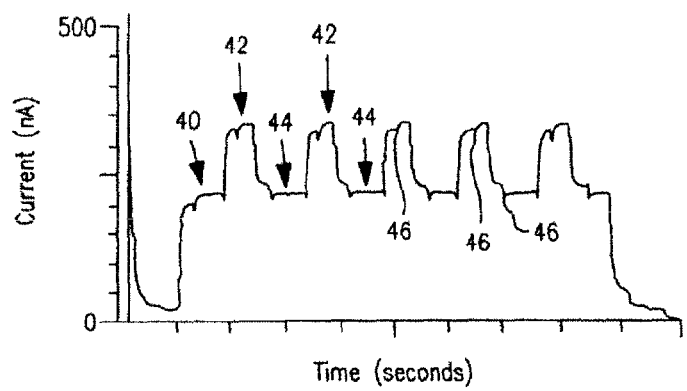
FIG. 2 is a plot of current versus time for an oxygen sensor of Fig.

Operation of such oxygen sensors is illustrated in FIG. 2. When the electrodes are polarized and a sample introduced to the sensor, the current produced by the oxygen in the sample is seen to be a relatively level value, depending on the percentage oxygen in the sample.

In FIG. 2, adapted from the '329 patent, which plots measured electrical current flow versus time, the response of a typical sensor, such as the one shown in FIG. 1, received a 12% oxygen aqueous calibration solution and produced a current at 40. Thereafter blood samples containing 20% oxygen produced the current shown at 42 and samples containing 12% oxygen produced current shown at 44. It is evident that a lower current is produced when a 12% oxygen samples is introduced than when a 20% oxygen sample is added to the sample chamber. Thus, the sensor produces a current flow that can be correlated to the oxygen content of a sample. As stated in the '329 patent, location 46 indicates anomalies caused by the sequential introduction of samples.

Figure 3:
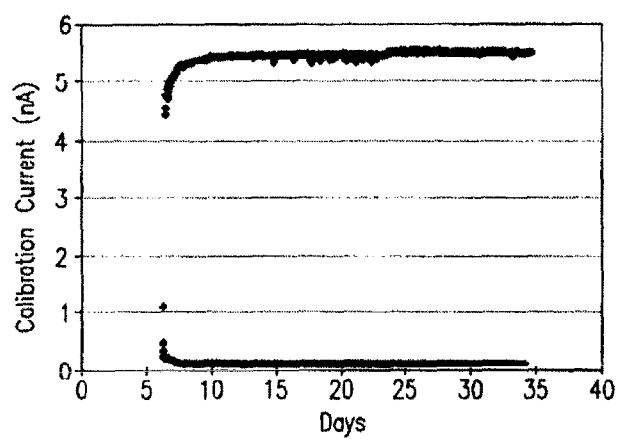
FIG. 3 is a typical plot of calibration current versus date for an oxygen sensor.
Figure 4:
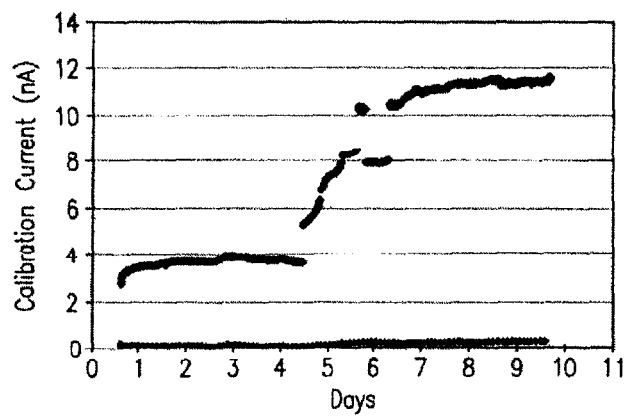
FIG. 4 is a typical plot of calibration current versus date for an oxygen sensor showing sudden failure.

When a sensor is used over an extended period of time the results are consistent, as is illustrated in FIG. 3, which plots the current produced over 35 days with two calibration samples representing high and low oxygen concentrations. That is, over many days the current produced is relatively consistent, as the sensor is calibrated on a regular basis to assure accuracy. However, when the sensor fails the current produced sharply increases, as shown in FIG. 4, where the zero oxygen calibration sample shows no change, but the calibration sample containing oxygen produced higher and erratic current after only 4-5 days.

The '329 patent suggests that failure of these oxygen sensors may occur due to contamination of the oxygen permeable membrane, or mechanical failure may result from delamination of the layered components. Another type of failure has been observed that is currently attributed to the formation of dendrites from the edges of the electrodes. These may result from several possible factors, including irregularities in the edges of the electrodes, metal impurities, or by-products from the electrochemical reduction of oxygen. Such sudden failures have been traced to the consistent presence of oxygen during the typical operating cycle that is employed.

In a typical operating protocol an oxygen sensor is in service 24 hours a day for 7 days a week. Blood samples may be tested as required, which may be from 1 to 100 to times each day. During the interim the sensor is idle, but kept under its standard polarization voltage, e.g. about –0.8 volts. At regular intervals (e.g. 30 minutes) aqueous calibrating solutions are measured. When a blood sample is introduced, its oxygen content is determined by using the results of the immediately preceding calibration. After the test is completed, the blood sample is removed and the sensor washed with an aqueous wash reagent solution typically containing surfactant, which remains in contact with the membrane when the senor is idle.

Experiments have been done in which the oxygen content of the wash solution is relatively low, e.g. about 20 mmHg, or relatively high, e.g. 700 mm Hg, in contrast with the more typical wash solution that will have about 110 mmHg oxygen. The calibration solutions also can have low or high oxygen contents. The results of the tests indicated that when the low oxygen content wash solution was used, that the useful life of the sensor was extended relative to sensors operated with high oxygen content wash solutions. It will be evident that excluding oxygen from the instrument is difficult and impractical.

EXAMPLE 1

Eight Rapidpoint 400 (Siemens Healthcare Diagnostics) were used to examine the effect of oxygen concentration in the wash solutions. Four instruments used a low oxygen wash solution (about 16.3 mmHg $O_2$) and four instruments used a high oxygen wash solution (about 700 mmHg $O_2$). Each instrument ran about 10 daily blood samples and was washed after each sample. Calibration with a 156 mmHg oxygen aqueous solution was done every half hour.

It was found that on the average the instruments washed with the low oxygen solution operated for about 10 weeks without failure, except for one instrument that experienced problems unrelated to the oxygen content of the wash solution. The instruments that were washed with the high oxygen solution all failed during calibration within about three weeks.

Extending Oxygen Sensor Life

While it appeared that using a low oxygen concentration wash solution would increase sensor life, excluding oxygen from the instrument was considered a possible, but impractical solution to the problem. Another method of avoiding the apparent effect of oxygen in the wash solution was investigated and found to significantly extend the useful life of the oxygen sensors. That is, reducing the effect of high oxygen wash solutions on sensor life by modulating the polarization voltage of the electrodes when they are not needed for calibration or for blood testing. This procedure avoids current being produced by the electrodes during about 96% of the time the sensor is in service. The electrodes are only fully polarized when being calibrated or when measuring samples.

In this method, the electrodes are polarized at −0.8 volts only during a measurement cycle, that is, during calibration and sample testing. At other times, the polarization voltage is about −0.1 volts, that is, during washing and in idle periods. While polarized at −0.1 volts essentially no electrical current is generated, since this voltage does not induce electrochemical reduction of oxygen. This was found to be true even when a high oxygen concentration wash solution was used to intentionally increase the number of sensor failures.

EXAMPLE 2

Eight Rapidpoint 400 instruments were tested to determine the effect of modulating polarization voltage. Each instrument used a high oxygen content wash solution. Four instruments were used as controls, that is they followed conventional protocols, including maintaining polarization of the electrodes at −0.8 volts throughout. The remaining instruments switched the polarization voltage from −0.8 volts to −0.1 volts except when the sensor was being calibrated or used to test samples. The control instruments showed failure of their sensors on the average at two weeks, while those instruments operated at −0.8 volts only during calibration and testing showed no sensor failures over eight weeks operation.

Figure 5:
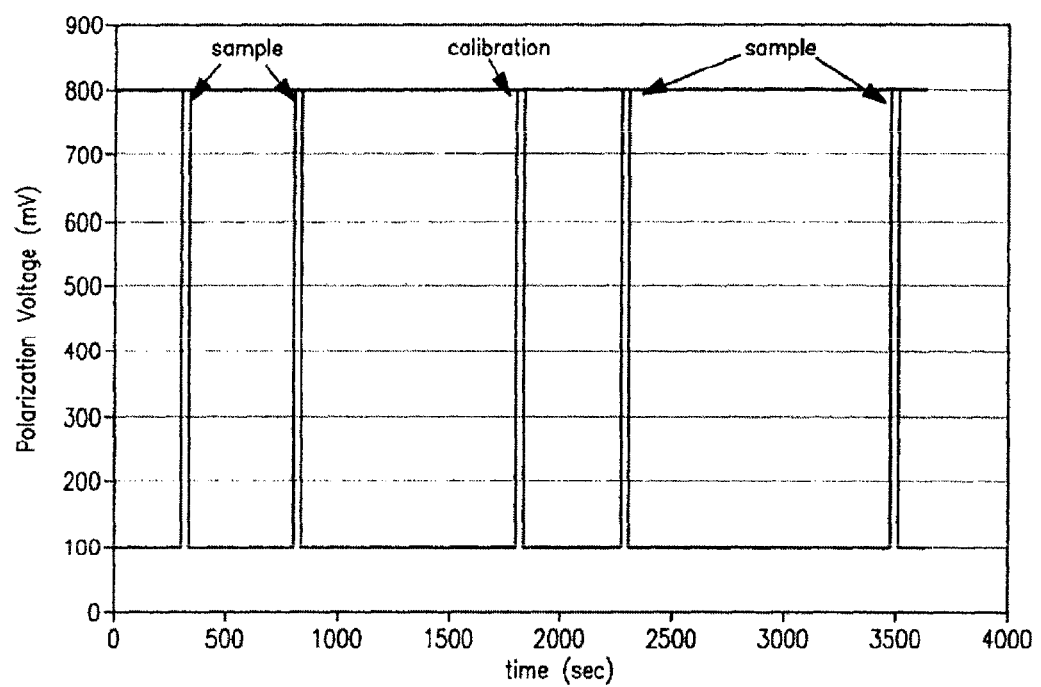
FIG. 5 is a diagram comparing the polarization used in previous practice with the present invention.

While several methods of reducing polarization voltage are possible, a preferred method of doing so employs the protocol illustrated in FIG. 5. Reducing the polarization voltage to some other values is also possible, although less desirable. For example, reducing the voltage to between −0.4 and 0 volts also should be beneficial. However, it is not desirable to switch off the polarization voltage entirely, although that would certainly minimize the oxygen effect. Experience has shown that such switching-off of polarization voltage can produce sensor failures.

In the electronic circuit, the polarizing voltage is typically created by taking isolated power and feeding it to a very precise reference diode in conjunction with a limiting resistor. This voltage, in turn, is further divided down by an appropriate resistor divider pair in order to create the correct polarization level needed for the polarization voltage (i.e. −800 mV). The modulation of this polarization voltage can be achieved by the addition of a parallel resistor and computer controlled optical isolator. The parallel resistor lowers the polarization voltage to −100 mV via computer command to the isolator. The optical feature of the isolator serves to isolate the computer hardware from the sensitive analog polarization signal.

In FIG. 5, the upper line represents operation of a sensor under conventional conditions, that is the sensor is maintained at a constant polarization of −0.8 volts (800 mV) through its service life. According to the invention the polarization of the sensor is modulated to −0.1 volts (100 mV) except when needed for measuring the oxygen content of a sample or when being calibrated. It will be evident that the sensor is polarized at its operating voltage for only a small fraction of its service life. It is preferable to maintain the low voltage during the idle periods to avoid problems associated with switching the polarization voltage electronic circuit completely on or off.

The technique applied to amperometric sensors for measuring the oxygen content of blood may be applied to the other such sensors for measuring the content of glucose, lactate, and the like in blood or other biological fluids. Improved service life in such sensors would be expected.

The invention claimed is:

1. A method of extending the service life of amperometric oxygen sensors having planar electrodes covered with a polymer electrolyte and a membrane permeable to oxygen, the improvement comprising operating said sensors at a polarization voltage suitable for measuring the oxygen content of a sample placed adjacent said oxygen permeable membrane only during the periods of time when said electrodes are being calibrated or testing samples, the polarization voltage being maintained, but systematically modulated to a lower polarization voltage at other times of idle instrument operation such that substantially no electrical current is produced by said electrodes.

2. The method of claim 1 wherein said operating polarization voltage is about −0.4 to −1.2 volts.

3. The method of claim 2 wherein said operating polarization voltage is about −0.8 volts.

4. The method of claim 1 wherein said polarization voltage is modulated to less than −0.4 volts except during periods of time wherein said electrodes are being calibrated or testing samples.

5. The method of claim 4 wherein the polarization voltage is modulated to about −0.1 volts except during periods of time wherein said electrodes are being calibrated or testing samples.

6. The method of claim 1 wherein said polarization voltage is modulated to a lower voltage for about 96% of the sensor's service life.

* * * * *